United States Patent [19]

Wojtech et al.

[11] 4,373,073
[45] Feb. 8, 1983

[54] PROCESS FOR THE PREPARATION OF GLYCIDYL ETHERS OF MONOHYDRIC OR POLYHYDRIC PHENOLS, THE GLYCIDYL ETHERS AND USE THEREOF

[75] Inventors: Bernhard Wojtech, Bad Soden am Taunus; Hans-Joachim Kiessling; Wilhelm Becker, both of Hamburg; Kurt Hermann, Idstein, all of Fed. Rep. of Germany

[73] Assignee: Hoechst Aktiengesellschaft, Frankfurt am Main, Fed. Rep. of Germany

[21] Appl. No.: 209,586

[22] Filed: Nov. 24, 1980

[30] Foreign Application Priority Data

Nov. 24, 1979 [DE] Fed. Rep. of Germany ....... 2947469

[51] Int. Cl.$^3$ ..................... C08G 59/06; C08G 59/08
[52] U.S. Cl. ..................................... 525/507; 528/89; 528/90; 528/93; 549/517
[58] Field of Search ........................... 528/89, 90, 93; 260/348.15; 549/517; 525/507

[56] References Cited

U.S. PATENT DOCUMENTS

| | | | |
|---|---|---|---|
| 2,943,096 | 6/1960 | Reinking | 260/348.15 |
| 3,221,032 | 11/1965 | Price et al. | 528/93 X |
| 3,336,342 | 8/1967 | Frank et al. | 260/348.15 |
| 3,417,050 | 12/1968 | Price et al. | 260/348.15 X |
| 3,980,679 | 9/1976 | Becker | 260/348.15 |
| 4,017,523 | 4/1977 | Vargiv et al. | 260/348.15 |
| 4,132,718 | 1/1979 | Vargiv et al. | 260/348.15 |
| 4,284,573 | 8/1981 | Arnett et al. | 260/348.15 |

Primary Examiner—Earl A. Nielsen
Attorney, Agent, or Firm—Hammond & Littell, Weissenberger and Muserlian

[57] ABSTRACT

Glycidyl ethers of monohydric or polyhydric phenols of high purity are obtained if hydrogen halide is eliminated from halohydrin ethers of the phenols in aqueous alkalis in the presence of one or more onium compounds selected from quaternary ammonium compounds having at least one aliphatic $C_{4-22}$ hydrocarbon radical, quaternary phosphonium compounds and tertiary sulphonium compounds as catalyst, or in the presence of those compounds which form in the reaction medium in situ, before the addition of the alkali, such onium compounds from the halohydrin ethers together with tertiary amines, tertiary phosphines or thioethers. In comparison with the known processes, the rate of dehydrohalogenation can thereby be significantly increased as a result of which an increase in production is achieved. Moreover, significantly purer reaction products are obtained by the avoidance of side reactions. The glycidyl ethers may be used as low-viscosity casting and coating resins in the form of coatings, adhesives, moulding materials, etc., and conventional hardeners can be employed. Due to their low viscosity the workability of the glycidyl ethers is considerably better and the capacity to absorb filling materials is greater. The extremely low content of easily saponifiable halogen results in an especially favorable corrosion behavior.

10 Claims, No Drawings

PROCESS FOR THE PREPARATION OF GLYCIDYL ETHERS OF MONOHYDRIC OR POLYHYDRIC PHENOLS, THE GLYCIDYL ETHERS AND USE THEREOF

This invention relates to a process for the preparation of glycidyl ethers of monohydric or polyhydric phenols by dehydrohalogenation of the products of the reaction of monohydric or polyhydric phenols with epihalohydrin by alkalis in the presence of specific catalysts. The invention also relates to the glycidyl ethers and to their use.

The reaction of monohydric or polyhydric phenols with excess epichlorohydrin to form chlorohydrin ethers and the conversion thereof, in the presence of alkaline-reacting substances, by elimination of hydrogen chloride into the corresponding glycidyl ethers is known. In so doing, it is possible to form the desired glycidyl ether directly (in a single-stage process), that is without separation of excess epichlorohydrin, from the intermediate product, i.e. the chlorohydrin ether. On the other hand, if the process is effected in two stages, this first provides for the separation of the chlorohydrin ether from excess epichlorohydrin, whereupon dehydrochlorination is effected with alkali liquor to form the glycidyl ether.

In the single-stage process the dehydrochlorination can be effected with sodium hydroxide solution, without previous isolation of the chlorohydrin ether, in the presence of water which dissolves the sodium chloride formed in the reaction and is separated therewith as a salt phase after the reaction has been completed. In the process according to Swiss patent specification No. 411,362, however, it is considered appropriate to work in the presence of 25 to 200% by weight of n-butanol in order to prevent losses of epichlorohydrin. However, the yield is thereby reduced and the expenditure on distillation is increased, thus making the process uneconomic.

Furthermore, it is also known to effect the dehydrochlorination of the catalytically formed chlorohydrin ether by alkali treatment with an aqueous alkali solution which contains 0.5 to 0.98 equivalents of alkali compound for each phenolic hydroxyl group and whose concentration is not greater than the saturation concentration of the salt obtained from the alkali treatment, at the temperature of the reaction mixture. According to this process the etherification mixture is treated with the aqueous alkali solution at a temperature of at least 50° C., the aqueous phase is separated, the epichlorohydrin is distilled from the organic phase and the residue is further treated with aqueous alkali solution (see German OLS No. 2,407,092).

In other single-stage processes, the water supplied e.g. by means of sodium hydroxide solution and the water formed by the reaction are removed continuously, during the addition of alkali, by azeotropic distillation with or without recycling of excess epichlorohydrin which is used as entrainer.

For example, the dehydrochlorination is effected according to German ALS No. 1,016,273 by adding an aqueous solution of at least 15% by weight of alkali hydroxide to a solution of a polyhydric phenol in at least 3 moles of epichlorohydrin for each phenolic hydroxyl equivalent of the phenol, the water and epichlorohydrin are distilled out of the reaction mixture, the distillation products are separated one from another and the epichlorohydrin is returned to the reaction mixture. The rate of supply of the alkali hydroxide solution and the rate of distillation are controlled so that the reaction mixture contains about 0.3 to 2% by weight of water.

Work can be carried out in a similar way, but with previous formation of the chlorohydrin ether, according to German OLS No. 2,028,136 if in a first stage excess epichlorohydrin is reacted with a polyphenol in the presence of a catalyst, for example a quaternary ammonium salt, in an amount of at least 5% relative to the amount of phenolic hydroxyl groups, to form chlorohydrin ether. In a second stage, an aqueous sodium hydroxide solution is added, which contains 0.80 to 0.99 equivalents of sodium hydroxide for each phenolic hydroxyl group, and water is removed by azeotropic distillation. The glycidyl ether is then subjected to further dehalogenation. The specified content of easily saponifiable chlorine for the products of the process lies between 0.20 and 0.75% by weight.

In these single-stage processes by-products are always produced which contaminate the glycidyl ethers due to the action of the alkali on the epichlorohydrin and this leads to losses of epichlorohydrin.

In two-stage processes an attempt is made to bypass the difficulties resulting from the side-reaction of epichlorohydrin in the alkaline medium by first catalytically reacting the monohydric or polyhydric phenol with the epichlorohydrin in a substantially anhydrous medium, then distilling off excess epichlorohydrin, and subsequently, in a second stage, after the addition of a solvent, converting the chlorohydrin ether with alkali liquor into the desired glycidyl ether. For example, according to U.S. Pat. No. 3,336,342, polyhydric phenols are reacted with epihalohydrins in the presence of sulphonium salts or sulphur-containing compounds which can react with epihalohydrin to give sulphonium salts, to form the corresponding halohydrins from which hydrogen halide is separated, after elimination of excess epihalohydrin, in order to obtain the desired epoxide compounds. This process requires at least 40 hours to form the chlorohydrin ethers. The excess epihalohydrin distilled off contains partly dihalohydrin and has to be treated separately before it can be used again as desired. The process is very time-consuming, complicated and uneconomic.

It is also known from U.S. Pat. No. 2,943,096 to convert polyhydric phenols and epichlorohydrin in the presence of condensation catalysts such as tetramethylammonium chloride or benzyltrimethylammonium chloride in a largely anhydrous medium into the corresponding chlorohydrin ethers. 26 Hours are required for this process. The processing of the reaction mixture is very expensive. The excess separated epichlorohydrin must, because of its content of dichlorohydrin, be treated by distillation and by means of sodium hydroxide solution to purify the epichlorohydrin so that it may be suitable for reuse. The isolated chlorohydrin ether, dissolved in a solvent mixture, is converted into the desired glycidyl ether by reaction with aqueous sodium hydroxide solution. Here, also, the individual process steps take up large amounts of time, so that it cannot be said that the process is very economical.

In a modification of one of the above-mentioned single-stage processes, according to German ALS No. 2,407,092, the total epihalohydrin or a part thereof is distilled from the etherification mixture and the residue is then treated with aqueous alkali solution. After separation of the phases, the aqueous fraction being abandoned, the remaining epihalohydrin and the epihalohydrin reformed during the alkali treatment are distilled from the organic phase and the residue is retreated with aqueous alkali solution. Because this treatment with the aqueous alkali solution has to be effected in several stages, the process becomes uneconomic due to the long vessel occupation time.

In all these above-described processes, pure glycidyl ether of the monohydric or polyhydric phenols which is ready for use is not obtained after the dehydrohalogenation, but only a crude product with a more or less large content of halohydrin ethers. Consequently, the crude product, generally dissolved in an organic solvent, must be subjected to a so-called re-dehalogenation with excess dilute aqueous sodium hydroxide solution. This entails a further operation, waste water is also produced and, moreover, some of the glycidyl groups are hydrolysed due to the effect of the alkali, as a result of which a loss of quality and reduction of the reactivity of the glycidyl ether takes place.

The dehydrochlorination of chlorohydrin ethers of monohydric or polyhydric phenols can be effected directly with aqueous alkali solutions with excess epichlorohydrin serving as solvent. In so doing, the dichlorohydrin obtained by re-epoxidation of the chlorohydrin ethers with epichlorohydrin is simultaneously converted again into epichlorohydrin.

The excess epichlorohydrin can, however, also be distilled out of the reaction mixture after reaction of the monohydric or polyhydric phenols with epichlorohydrin. In this case, the dichlorohydrin contained in the distillate and originating from the re-epoxidation reaction must be converted, before the distillate is used again, into epichlorohydrin by treatment with alkalis. The reaction products, chlorohydrin ethers of the monohydric or polyhydric phenols, are more or less of high-viscosity and, before elimination of the HCl by aqueous alkalis, are dissolved in an inert, largely water-insoluble, organic solvent such as methyl isobutyl ketone, benzene, toluene or xylene. After phase separation, the solvent is distilled from the glycidyl ether formed and is returned to the process. It is appropriate not to increase the concentration of alkali liquor used above 20% in order to prevent salt precipitation. The two reaction materials that is, chlorohydrin ethers of the monohydric or polyhydric phenols which are dissolved in the solvent and the aqueous alkalis which are contained in the two phases immiscible with one another, come in contact with one another only at the interface. The course of the reaction is considerably hamperedby the phase transition. This becomes noticeable in a disturbing way especially at low concentrations, that is at the end of the reaction, resulting in a constant decrease of the reaction rate. According to German ALS No. 1,103,580 an increase in the phase transmittance and a resulting acceleration of the reaction rate may be achieved by the addition of a water-soluble organic component such as ethanol, acetone, dioxan and the like to the water-insoluble solvent. It is disadvantageous that due to the absorption of a part of the water-soluble components into the aqueous phase there arise significant losses of solvent which necessitate additional measures for recovery.

It has now been found that glycidyl ethers of monohydric or polyhydric phenols of high purity can be obtained if the elimination of hydrogen halide from halohydrin ethers of monohydric or polyhydric phenols in aqueous alkalis is effected, according to the present invention, in the presence of one or more onium compounds, preferably those with surface active properties, for example cation-active quaternary ammonium compounds, as catalysts for the hydrogen halide elimination. In comparison with known processes, the rate of dehydrohalogenation can thereby be accelerated many times, as a result of which the vessel occupation time is considerably reduced and, by the avoidance of side-reactions, such as hydrolysis of glycidyl groups already formed, significantly purer reaction products are obtained.

Thus, the present invention provides a process for the preparation of glycidyl ethers of monohydric or polyhydric phenols by reaction of a phenol with an epihalohydrin and subsequent dehydrohalogenation of the halohydrin ether thereby produced with aqueous alkali, wherein the dehydrohalogenation is effected in the presence of:

(a) a catalyst derived from one or more onium compounds, the substituents thereof consisting of hydrocarbon radicals, selected from the group consisting of
1. quaternary ammonium compounds with at least one aliphatic $C_{4-22}$ hydrocarbon radical,
2. quaternary phosphonium compounds, and
3. tertiary sulphonium compounds; or
(b) compounds which will form in the reaction medium *in situ*, before the addition of the alkali, such an onium compound which is derived from the halohydrin ethers and corresponding tertiary amines, tertiary phosphines or thioethers.

The invention also provides the glycidyl ethers prepared according to the above-process as well as their use as coating and casting resins.

The halohydrin ethers are prepared in conventional manner by catalytic condensation from at least one phenol and epihalohydrin and are dissolved either in excess epihalohydrin or, after evaporating off the ecess epihalohydrin, in an inert organic solvent.

Examples of monohydric or polyhydric phenols which may be used for preparing the halohydrin ethers include phenol, o-, m- and p-phenylphenol, the various amylphenol, octylphenol and cresol isomers; 1,2,3-, 1,2,4-, 1,2,5-, 1,3,4- and 1,3,5-xylenol; p-tert.-butylphenol, o-, m- and p-nonylphenols; pyrocatechol; resorcinol; hydroquinone; 1,4- and other dihydroxynaphthalenes; 4,4'-, 2,2'- and other dihydroxydiphenyls; 2,2'-, 2,4'- and 4,4'-dihydroxydiphenylmethane, either individually or in admixture (also known as bisphenol F); 4,4'-dihydroxydibenzyl; 4,4'-dihydroxydiphenylsulphone; substituted dihydroxydiphenylmethanes, such as are obtained by acid condensation of phenols with aldehydes or ketones, especially 4,4'-dihydroxydiphenyl-2,2 -propane which can be prepared from phenol and acetone; and dihydroxydiphenylcyclohexane.

There may also be mentioned as further examples of phenols:
4,4'-dihydroxy-3,3',5,5'-tetramethyldiphenylmethane and -2,2-propane;
4,4'-dihydroxy-3,3',5,5'-tetra-p-tert.-butyldiphenylmethane, -2,2-propane and -cyclohexane;
4,4'-dihydroxy-3,3'-dimethyl-5,5'-di-p-tert.-butyldiphenylmethane, -2,2-propane and -cyclohexane; and
4,4'-dihydroxy-3,3',5,5'-tetraamyldiphenylcyclohexane.

The polyhydric phenols which may be used as starting materials may contain, in addition to the phenolic hydroxyl groups, also other substituents or functional groups in the molecule, for example hydrocarbon radicals, ether groups, ester groups, halogen atoms, further hydroxyl groups and the like, provided that the desired reaction is not affected thereby. Accordingly, for example tetrabromobisphenol, tetrachlorobisphenol, chlorohydroquinones, methyl resorcinol and phloroglucinol, come under consideration.

Other examples of polyhydric phenols which may be used include novolak resins which are obtained by acid-catalysed condensation of phenol, p-cresol or other substituted phenols with aldehydes such as formaldehyde, acetaldehyde, crotonaldehyde, isobutyraldehyde, isononylaldehyde, etc.; condensates of phenols with cardanol; condensates of phenols with aliphatic diols; and condensates of phenols with unsaturated fatty oils.

The above-mentioned list of compounds suitable as starting materials is contained e.g. in the book "Epoxide compounds and epoxide resins" by A. M. Paquin, Springer-Verlag, 1958, pages 256–307. Phenol, p-tert.-butylphenol, 4,4'-dihydroxydiphenol-2,2-propane or -methane, tetrabromobisphenol and phenol novolaks are preferably used.

In one embodiment of the process, a mixture of 0.60 to 0.99 moles of 4,4'-dihydroxydiphenyl-2,2-propane and 0.40 to 0.01 moles of a diphenol selected from the group of the above-mentioned compounds, especially hydroquinone, resorcinol, bisphenol F and the above-mentioned novolak resins, is used to prepare diglycidyl ethers having a low viscosity (6000 to 16000 mPa.s/25° C.), in order to prevent crystallisation of the products during lengthy storage in cool places.

Examples of epihalohydrins which may be used include epibromohydrin and 1,4-dichloro-2,3-epoxybutane, but preferably epichlorohydrin. The epihalohydrin acts not only as a reaction component, but also as the solvent for the monohydric, or polyhydric phenol and the ether formed.

The solution of halohydrin ether is mixed with the dilute aqueous alkali solution and with the onium catalyst, and the halohydrin ether is reacted in this two-phase system with vigorous stirring, conveniently at an elevated temperature, with hydrogen halide elimination to form the desired glycidyl ether.

Quaternary ammonium compounds are among the most readily available and therefore most usual cation-active onium compounds. They are surface active (interfacially active) materials in which the higher-molecular hydrophobic radical causing the surface activity is located in the cation upon dissociation in aqueous solution. All the cation-active compounds contain a basic onium group, for example basic nitrogen in a quaternary ammonium compound, with one or more higher-molecular hydrophobic radicals. On being dissolved in water, they preferably concentrate at the surface or, in the additional presence of a lipophilic phase, at the phase interface.

The catalytic activity in the process according to the invention increases e.g. with a increasing chain length of the substituents of the ammonium nitrogen atom. Thus, tetramethylammonium chloride as well as trimethylbenzylammonium chloride, the preferred condensation catalysts in the reaction of phenols and epichlorohydrin, are substantially less active than e.g. tetrabutylammonium chloride. This is, in turn, not so active as cation-active compounds with longer-chained alkyl radicals, for example distearyldimethylammonium chloride or coconut alkyldimethylbenzylammonium chloride.

Examples of ammonium compounds which may be used as dehydrohalogenation catalysts in the process include those having the general formula

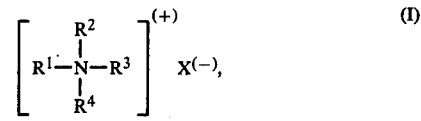

in which $R^1$, $R^2$, $R^3$ and $R^4$, which may be the same or different, each represents an alkyl, cycloalkyl, alkenyl, aryl or aralkyl group with up to 18, preferably 1 to 12 carbon atoms and which may optionally contain one or more hydroxy or ether groups with at most 4 carbon atoms but at least one of $R^1$, $R^2$, $R^3$ and $R^4$ is a branched or unbranched alkyl or alkenyl group with 4 to 22, preferably 8 to 22 carbon atoms; and $X^{(-)}$ represents a monovalent anion, preferably a halogen anion such as a chloride, bromide, iodide or sulphonate anion. The chloride ion is especially preferred.

Examples of phosphonium and tertiary sulphonium compound, which may be used in the process, include those having the formula

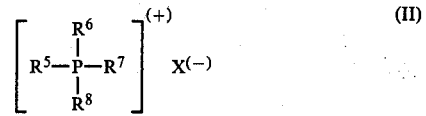

and

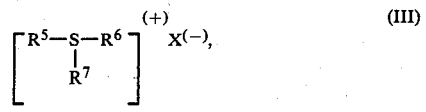

in which $R^5$, $R^6$, $R^7$ and $R^8$, which may be the same or different, each represents an alkyl, cycloalkyl, alkenyl, aralkyl or aryl group each with 1 to 12 carbon atoms, and which optionally contain one or more hydroxyl or ether groups, with at most 4 carbon atoms, and $X^{(-)}$ is as defined above and are used in the same way as the above described quaternary ammonium compounds.

Cation-active onium catalysts may generally be produced by "peralkylation" (by which is also meant the reaction with corresponding aryl compounds) of tertiary amines, tertiary phosphines and thioethers, especially dialkylsulphides. The higher-molecular hydrophobic radical may be derived from the basic substances as well as from the alkylating agent. There can be used as "alkylating agent," instead of alkyl chlorides, for example also halogenalkyl alcohols or halogenalkyl ethers, as well as the corresponding aryl compounds.

It has been found that the halohydrin ethers may also serve as "alkylating agents" and result in highly active catalysts by reaction with tertiary amines, tertiary phosphines or thioethers. Catalyst preparation can therefore be effected *in situ* directly in the reaction vessel in the halohydrin ethers before the dehydrohalogenation. After catalyst formation which is effected at elevated temperature to increase the rate of reaction, the dehydrohalogenation is effected in the conventional way in the presence of aqueous alkalis.

The quantity of catalyst in the dehydrohalogenation reaction is e.g. 0.01 to 10% by weight, preferably 0.1 to 5% by weight, relative to the amount of halohydrin ether.

Preferred quaternary ammonium catalysts are e.g. octyltrimethyl- or soy-alkyltrimethyl- and distearyl-dimethyl-ammonium chloride or compounds with a long-chained radical and a benzyl group such as coconut alkylbenzyldimethylammonium chloride.

Preferred quaternary phosphonium compounds are e.g. triphenylethylphosphonium bromide, tetramethyl-, tetraphenyl- and tetrabenzyl- phosphonium chloride.

Examples of sulphonium compounds include trimethylsulphonium iodide and dibenzylmethylsulphonium bromide.

Tertiary amines, phosphines and dialkylsulphides which form onium salts of the above type in the reaction medium with the halohydrin ethers include e.g. tri-n-butylamine, tri-tert.-butylamine, triisooctylamine, octyldimethylamine, soy-alkyldimethylamine, distearylmethylamine, triphenylphosphine, trimethylphosphine, triethylphosphine, tripropylphosphine, tributylphosphine, tribenzylphosphine, dibenzylsulphide. benzylethylsulphide, benzylbutylsulphide and diethylsulphide.

The dehydrohalogenation is appropriately effected with aqueous alkalis such as sodium or potassium hydroxide, but preferably sodium hydroxide. The concentration of the alkaline solution is to be selected in the dehydrohalogenation so that precipitation of salt deposits which hamper phase separation are avoided. Preferably, the concentration is no higher than 18% by weight relative to sodium hydroxide. In general, work is carried out with stoichiometric quantities; appropriately, the hydrogen halide elimination can be effected by using an up to 20% excess above the stoichiometrically necessary quantity of base.

Critical for the quantity of alkali required is the content of active (saponifiable) halogen, for example chlorine in the chlorohydrin ester, or, if work is carried out in excess epichlorohydrin, the number of hydroxyl groups in the phenolic starting product. The molar ratio of the quantity of alkali required to the number of hydrolysable halogen atoms or to the number of phenolic hydroxyl groups is generally 0.95 to 1.5:1, preferably 1.0 to 1.2:1.

The dehydrohalogenation of the halohydrin ether to give the diglycidyl ether can be effected in similar manner to that of the known two-stage process, after distilling off the epichlorohydrin, in an inert solvent, for example in toluene, xylene, higher ketones such as methyl isobutyl ketone, higher alcohols such as n- or iso-butanol or mixtures of these solvents.

It is advantageous to work at an elevated temperature of from 40° and 95° C., preferably from 70° to 90° C. Since this is a two-phase reaction, the reaction mixture is conveniently stirred vigorously.

If the excess epichlorohydrin is not separated after the single-stage process, it is not necessary to add an inert solvent to dilute the halohydrin ether. In this case, the dehydrohalogenation should be effected at not too high a temperature, preferably at 40° to 60° C. in order to prevent side reactions of the epihalohydrin in the alkaline aqueous medium. The lower reactivity at low temperature necessitates a higher concentration of catalyst. To keep any losses of epihalohydrin which may occur due to side reactions as small as possible, it is also recommended to allow the sodium hydroxide solution to flow only slowly into the vigorously stirred reaction mixture, for example, in proportion as it is reacted. In this way, too high a concentration of alkali in the reaction medium is avoided.

The process according to the invention may be operated continuously or batchwise. In continuous operation, the two phases (organic phase and aqueous alkali liquor) can be conveyed in counterflow or in synchronous flow both in one stage or in several stages.

The distribution of the catalyst between both phases in synchronous flow operation (cascade operation) in several stages gives a better catalytic effect and therefore a better yield than in counterflow operation.

At the end of the dehydrohalogenation, the two phases are separated on the basis of their density differences, and the glycidyl ether may be obtained from the organic phase after distilling off the solvent. The solvent may be recycled in the process. The glycidyl ether may be liberated from remaining solvent, advantageously under reduced pressure and at temperatures up to 150° C., preferably up to 120° C., and from salt residues by filtration. The glycidyl ethers are characterized by determination of their viscosity, their epoxide equivalent and their content of hydrolysable halogen (according to ASTM D 1226-60T).

The glycidyl ethers of monohydric or polyhydric phenols which are obtained according to the above-mentioned process may be employed as such or optionally together with suitable additives, as low-viscosity casting and coating resins with the use of conventional hardeners such as amines, polycarboxylic acids or their anhydrides in coatings, adhesives, moulding materials, etc. Because of their low viscosity a considerably better workability and a substantially higher capacity for absorbing filling materials are provided. Due to the extremely low content of easily saponifiable halogen, the glycidyl ethers are also characterised by an especially favourable corrosion behaviour, which is important especially in processing with metallic objects.

The invention will now be illustrated in the following Examples, in which T always represents parts and % always represents percentage by weight.

EXAMPLE 1

(a) Preparation of bisphenol A-dichlorohydrin ether

228 T of 4,4'-dihydroxydiphenyl-2,2-propane (bisphenol A) and 920 T of epichlorohydrin were mixed and blended with 5.2 T of a choline chloride solution (70% in water) for each mole of bisphenol A. The mixture was refluxed for 5 minutes at about 120° C., excess epichlorohydrin was subsequently distilled off and the epichlorohydrin residue still remaining was removed under reduced pressure at 120° to 125° C. The reaction yield was about 98% relative to the phenolic hydroxyl groups. Content of hydrolysable chlorine 8.3%, epoxide equivalent 390 to 410, viscosity 80 Pa.s/25° C.

(b) Dehydrochlorination of bisphenol-A-dichlorohydrin ether to diglycidyl ether

A 50% solution of the dichlorohydrin ether from (a) in xylene was mixed with enough 7% aqueous sodium hydroxide solution to ensure that the molar ratio of NaOH to hydrolysable chlorine was 1.09:1.0. 0.2% Distearyldimethylammonium chloride (75% solution in isopropanol-water 2:1), relative to the quantity of solvent-free dichlorohydrin ether used, had previously been added as catalyst to the sodium hydroxide solution. The reaction mixture was heated with vigorous stirring for 90 minutes at 80° C. and then quickly cooled to room temperature. After stirring had been stopped, the phases separated rapidly and were isolated. The xylene was removed from the organic xylene phase by distillation first under normal pressure and then under reduced pressure with increasing temperature to 120° C. The glycidyl ether formed contained 0.16% hydrolysable chlorine, epoxide equivalent 186, viscosity 9.03 Pa.s/25° C.

EXAMPLES 2 to 6

Example 1 was repeated with the difference that other catalysts were used in the dehydrochlorination step. Table 1 gives the quantitive ratios of the catalysts, relative to the solvent-free quantity of dichlorohydrine ether, reaction conditions and characteristics of the glycidyl ethers obtained. In Examples 5 and 6 the catalyst was produced "in situ," that is tertiary amine or dialkylsulphide were introduced to the 50% solution of dichlorohydrin ether and the mixture was heated, in each case, for 1 hour to 80° C. to quaternate the tertiary amine or to form the sulphonium of the thioether respectively, whereupon the sodium hydroxide solution was added.

chloride as catalyst. The molar ratio of sodium hydroxide introduced to phenolic hydroxyl groups introduced was 1.15:1. At the beginning of the reaction, 40 T of alkali liquor, that is 14% of the total quantity of alkali liquor, with the total catalyst, that is 2.4 T of a solution of 75% distearyldimethylammonium chloride in isopropanol-water (2:1), were introduced. The remaining 86% of sodium hydroxide liquor (247.5T) were added slowly over 105 minutes with vigorous stirring and the mixture was then stirred for a further 15 minutes to complete the reaction. The phases which formed after stirring was stopped were separated and the epichlorohydrin was distilled from the organic phase under reduced pressure at a temperature increasing to 110° C. The yield of diglycidyl ether was 145 T, hydrolysable chlorine 0.15% epoxide equivalent 181, viscosity 8.12 Pa.s/25° C.

EXAMPLE 9

Example 8 was repeated with 100 T of p-tert.-butylphenol, 333 T of epichlorohydrin and 3.1 T of a solution

TABLE 1

| Example | 2 | 3 | 4 | 5 | 6 |
| --- | --- | --- | --- | --- | --- |
| Catalyst | Coconut alkylbenzyldimethylammonium chloride | Tetraphenylphosphonium chloride | Trimethylsulphonium iodide | Triisoctylamine | Dibenzylsulphide |
| Quantity of catalyst (%) | 1 | 1.4 | 1.4 | 1 | 1.4 |
| Reaction conditions | 20', 80° C. | 30', 80° C. | 20', 80° C. | 20', 80° C. | 20', 80° C. |
| Hydrolysable chlorine (%) | 0.2 | 0.12 | 0.11 | 0.03 | 0.05 |
| Epoxide equivalent | 186 | 184 | 181 | 188 | 183 |
| Viscosity Pa.s (25° C.) | 9.40 | 9.53 | 9.67 | 11.6 | 13.8 |

EXAMPLE 7

For the continuous preparation of bisphenol A-diglycidylether, a solution of 50% dichlorohydrin ether in xylene (prepared as in Example 1a) was mixed with 1.25% distearyldimethylammonium chloride in the form of a 75% solution in isopropanol-water (2:1) (relative to the dichlorohydrine ether). This feed solution (=S) was subsequently introduced, together with 7% aqueous sodium hydroxide solution, into a two-stage agitated cascade (synchronous flow) vessel so that a molar ratio of NaOH to hydrolysable chloride of 1.1 to 1.0 was obtained (flow ratio of S to sodium hydroxide=1.5 to 1.0). The temperature of the two agitator vessels was 80° C. and the dwell time in each vessel was 7 minutes. The characteristics of the diglycidyl ether obtained were: 0.20% hydrolysable chlorine, epoxide equivalent 188, viscosity 9.35 l Pa.s/25° C.

EXAMPLE 8

A mixture of 100 T of 4,4'- dihydroxydiphenyl-2,2-propane (bisphenol A), 406 T of epichlorohydrin and 2 T of a solution of 50% tetramethylammonium chloride in water (molar ratio of 1:10:0.021) was heated to 100° C. with stirring for 3.5 hours. 98% of the bisphenol was reacted (as shown by UV spectral analysis). The reaction mixture (bisphenol A-dichlorohydrin ether in excess epichlorohydrin) was cooled to 50° C. and the dehydrochlorination was effected at this temperature by the addition of 287.5 T of 14% sodium hydroxide solution in the presence of distearyldimethylammonium of 50% tetramethylammonium chloride in water (molar ratio 1:10:0.021) and heated to 100° C. until at least 98% of the phenolic hydroxyl groups had reacted. The reaction mixture was cooled to 50° C. and dihydrochlorination was effected with 218.5 T of 14% sodium hydroxide solution in the presence of 2.4 T of distearyldimethylammonium chloride (75% in isopropanol-water, 2:1). Yield 134 T of p-tert.-butylglycidyl ether, hydrolysable chlorine 0.12%, epoxide equivalent 212, viscosity of 17 mPa.s/25° C.

EXAMPLE 10

Example 8 was repeated with 100 T of bisphenol F (isomeric mixture), 555 T of epichlorohydrin and 2.3 T of a solution of 50% tetramethylammonium chloride in water (molar ratio 1:12:0.021) and heated to 100° C. until at least 98% of the phenolic hydroxyl groups had reacted. The reaction mixture was cooled to 50° C. and dehydrochlorination was effected with 329 T of 14% sodium hydroxide solution in the presence of 2.4 T of distearyldimethylammonium chloride (75% in isopropanol-water, 2:1). Yield 149 T of the glycidyl ether of bisphenol F (isomeric mixture); hydrolysable chlorine 0.17%, epoxide equivalent 172, viscosity 2120 mPa.s/25° C.

EXAMPLE 11

Example 8 was repeated with a mixture of 59.5 T of tetrabromobisphenol, 40.5 T of bisphenol A, 313 T of epichlorohydrin and 1.3 T of a solution of 50% tetramethylammonium chloride in water (molar ratio 1:12:0.021) and heated to 100° C. until at least 97% of the phenolic hydroxyl groups have reacted. The reaction mixture was cooled to 50° C. and the dihydrochlorination was effected with 188.6 T of 14% sodium hydroxide solution in the presence of 2.4 T of distearyldimethylammonium chloride (75% in isopropanol-water, 2:1). Yield 129 T of the viscous mixed glycidyl ether of tetrabromobisphenol and bisphenol A; hydrolysable chlorine 0.13%, epoxide equivalent 249, viscosity 750 Pa.s/25° C.

EXAMPLE 12

900 T of phenol were heated to 100° C. with 9 T of crystallised oxalic acid dissolved in 18 T of water. At 100° C. 369 T of 37% formaldehyde solution were added at reflux and heated to 120° C., an aqueous distillate mainly being removed by using a separator. Under reduced pressure at 20 mmHg the mixture was heated to 150° C., excess phenol largely being removed. By steam distillation under reduced pressure at 140° to 150° C. the content of free phenol was subsequently reduced to 0.5%.

According to the particulars of Example 8, 100 T of the novolak described above, 555 T of epichlorohydrin and 4.6 T of a solution of 50% tetramethylammonium chloride in water (molar ratio 1:12:0.042) were refluxed to 118° to 120° C. until at least 96% of the phenolic hydroxyl groups have reacted. The reaction mixture was cooled to 50° C. and the dehydrochlorination was effected with 324 T of 14% sodium hydroxide solution in the presence of 2.4 T of distearylmethylammonium chloride (75% in isopropanol-water, 2:1). Yield 145 T of the novolak glycidyl ether; hydrolysable chlorine 0.14% epoxide equivalent 173, viscosity 23600 mPa.s/52° C.

Comparison tests to show the technical advance achieved

The reaction rate of dehydrochlorination without and with catalyst was compared by reference to the hydrolysable chlorine fraction remaining in the diglycidyl ether.

Two-stage process

Example 1 was repeated with and without various catalysts, the reaction time generally amounting to 20 minutes during dehydrochlorination. See Table 2.

TABLE 2

| Example | Catalyst Type | Quantity (%) | Reaction time (minutes) | Hydrolysable chlorine (%) |
|---|---|---|---|---|
| 13 | Tetrabutylammonium chloride | 0.20 | 20 | 0.45 |
| 14 | Distearyldimethylammonium chloride (75% in isopropanol-water, 2:1) | 0.20 | 20 | 0.20 |
| 15 | Distearyldimethylammonium chloride (75% in isopropanol-water, 2:1) | 2.0 | 5 | 0.20 |
| Comparison 1a | Without catalyst | — | 20 | 4.1 |
| Comparison 1b | Without catalyst | — | 500 | 1.2 |
| Comparison 2 | Tetraethylammonium chloride | 0.20 | 20 | 3.6 |
| Comparison 3 | Benzyltrimethylammonium chloride | 0.20 | 20 | 3.4 |

Whereas in the dehydrochlorination without catalyst a high content of hydrolysable chlorine was still present even after a reaction time of 500 minutes, it is possible, by means of the process according to the invention, with certain catalysts to obtain largely chlorine-free products within a short time. The superiority of the catalysts added according to the invention is especially shown by the considerable reduction of the reaction time when higher quantities of catalyst are used. Condensation catalysts which are used in the preparation of the chlorohydrin ethers display only a small effectiveness in the dehydrochlorination.

Single-stage process

Example 8 was repeated without catalyst. Table 3 sets out the values obtained in comparison with Example 8.

TABLE 3

| Example | Catalyst Type | Quantity (%) | Reaction time (minutes) Addition | Reaction time (minutes) Total | Hydrolysable chlorine (%) |
|---|---|---|---|---|---|
| 8 | Distearyldimethylammonium chloride (75% in isopropanol-water, 2:1) | 2.40 | 105 | 120 | 0.15 |
| Comparison 4 | Without catalyst | — | 105 | 120 | 2.1 |

It is clear from the tests of Table 3 that because of the presence of dehydrohalogenation catalyst in the single-stage process glycidyl ethers with a very low content of hydrolysable chlorine are obtained.

We claim:

1. A process for the preparation of glycidyl ethers of phenols which comprises the steps of reacting (A) a monohydric or polyhdric phenol with an epihalohydrin in the presence of a conventional condensation catalyst to form a halohydrin ether and (B) adding thereto aqueous alkali and one of the components.
   (a) a catalyst derived from at least one onium compound the substituents of which consists of hydrocarbon radicals selected from the group consisting of
   (1) quarternary ammonium compounds with at least one aliphatic $C_4$–$C_{22}$ hydrocarbon radical, and,
   (2) tertiary sulphonium compounds; and
   (b) compounds which will form in the reaction mixture in situ before the addition of the alkali, such an onium compound which is derived from the hylohydrin ethers and a corresponding substance selected from the group consisting of tertiary amines, teritary phosphines and thioethers and subjecting this mixture in the presence of an inert solvent or excess unreacted epihalohydrin to dehydrohalogenation of said halohydrin ether, the onium compound having a monovalent anion.

2. A process as set forth in claim 1 wherein the sum of the carbon atoms in the radicals of the quaternary ammonium compounds is at least 11.

3. A process as claimed in claim 1 or 2 wherein the monovalent anion is a halogen or sulphonate anion.

4. A process as claimed in claim 1 or 2 wherein at least one aliphatic hydrocarbon radical has 8–12 carbon atoms.

5. A process as claimed in claim 1, wherein the catalyst is a quarternary ammonium compound of the formula

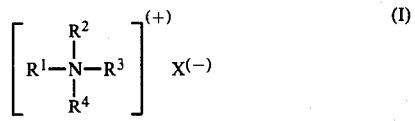

in which at least one of $R^1$, $R^2$, $R^3$ and $R^4$ represents an alkyl or alkenyl group with 4 to 22 carbon atoms and the other each represent a member selected from the group consisting of alkyl, cycloalkyl, alkenyl, aryl and aralkyl groups having up to 18 carbon atoms and derivatives thereof containing at least one hydroxyl or ether group with at most 4 carbon atoms and $X^{(-)}$ represents a monovalent anion.

6. A process as claimed in claim 1 wherein the catalyst is a tertiary sulphonium compound of the formula

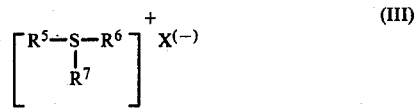

in which $R^5$, $R^6$ and $R^7$ each represents a member selected from the group consisting of alkyl, cycloalkyl, alkenyl, aralkyl or aryl group each with 1 to 12 carbon atoms and derivatives thereof containing at least one hydroxyl or ether group with at most 4 carbon atoms and $X^{(-)}$ represents a monovalent anion.

7. A process as claimed in claim 1 wherein the dehydrohalogenation catalyst is used in a quantity of 0.01 to 10 percent by weight, relative to the amount of halohydrin ether.

8. A process as claimed in claim 1 wherein the alkali is added in an amount such that its ratio to the quantity of hydrolyzable halogen or the number of hydroxyl groups in the starting phenol is 0.95 to 1.5:1.

9. A process as claimed in claim 1 wherein the temperature in the dehydrohalogenation reaction of a two-stage process is 40° to 95° C. and of a single-stage process is 40° to 60° C.

10. A process as claimed in claim 1, wherein the alkali in the dehydrohalogenation step is sodium hydroxide and the ratio is 1.0 to 1.2:1.

* * * * *

UNITED STATES PATENT AND TRADEMARK OFFICE
CERTIFICATE OF CORRECTION

PATENT NO. : 4,373,073
DATED : February 8, 1983
INVENTOR(S) : BERNHARD WOJTECH ET AL.

It is certified that error appears in the above-identified patent and that said Letters Patent is hereby corrected as shown below:

Column 4, line 37: "ecess" should read -- excess --.
Column 6, line 23: "compound" should read -- compounds --.
Column 7, line 36: "ester" should read -- ether --.
Column 11, line 8: "glycidly" should read -- glycidyl --.
Column 12, line 46: after "of" insert -- a --.

Signed and Sealed this

Twelfth Day of July 1983

[SEAL]

Attest:

GERALD J. MOSSINGHOFF

Attesting Officer

Commissioner of Patents and Trademarks